United States Patent
Okabe et al.

(10) Patent No.: US 10,585,476 B2
(45) Date of Patent: Mar. 10, 2020

(54) APPARATUS OPERATION DEVICE, APPARATUS OPERATION METHOD, AND ELECTRONIC APPARATUS SYSTEM

(71) Applicant: FUJIFILM Corporation, Tokyo (JP)

(72) Inventors: Yuuki Okabe, Tokyo (JP); Mayuko Ikuta, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 2 days.

(21) Appl. No.: 15/898,368

(22) Filed: Feb. 16, 2018

(65) Prior Publication Data

US 2018/0173306 A1 Jun. 21, 2018

Related U.S. Application Data

(63) Continuation of application No. PCT/JP2016/070073, filed on Jul. 7, 2016.

(30) Foreign Application Priority Data

Sep. 4, 2015 (JP) ................. 2015-174575

(51) Int. Cl.
*G06F 3/01* (2006.01)
*G06F 3/16* (2006.01)
(Continued)

(52) U.S. Cl.
CPC .............. *G06F 3/013* (2013.01); *A61B 1/04* (2013.01); *A61B 5/1114* (2013.01);
(Continued)

(58) Field of Classification Search
CPC ... G06F 3/01; G06F 3/012; G06F 3/16; G06F 3/013; G06F 3/015; G06F 3/017; G06F 3/0346; G06F 3/038
See application file for complete search history.

(56) References Cited

U.S. PATENT DOCUMENTS

| 6,677,969 B1 | 1/2004 | Hongo |
| 2002/0110252 A1 | 8/2002 | Liu |

(Continued)

FOREIGN PATENT DOCUMENTS

| JP | H04-372012 A | 12/1992 |
| JP | H10-198476 A | 7/1998 |

(Continued)

OTHER PUBLICATIONS

Extended European Search Report issued by the European Patent Office dated Aug. 13, 2018, which corresponds to EP16841280.7-1216 and is related to U.S. Appl. No. 15/898,368.

(Continued)

*Primary Examiner* — Md Saiful A Siddiqui
(74) *Attorney, Agent, or Firm* — Studebaker & Brackett PC

(57) ABSTRACT

An apparatus operation device includes a line-of-sight detecting unit that detects a line of sight of a user, a neck-mounted terminal that is mounted around a neck of the user and detects a motion of the neck of the user, a determining unit that determines, based on the line of sight that has been detected and the motion of the neck that has been detected, at least one of an electronic apparatus as a target apparatus to be operated or operation details, and an apparatus control unit that controls the electronic apparatus as the target apparatus in accordance with the determination.

19 Claims, 15 Drawing Sheets

(51) Int. Cl.
    *G10L 15/22*     (2006.01)
    *G06F 3/038*     (2013.01)
    *A61B 1/04*     (2006.01)
    *G06F 3/0346*     (2013.01)
    *A61B 5/00*     (2006.01)
    *A61B 5/11*     (2006.01)
    *G06K 9/00*     (2006.01)

(52) U.S. Cl.
    CPC .......... *A61B 5/1128* (2013.01); *A61B 5/6822* (2013.01); *A61B 5/7475* (2013.01); *G06F 3/01* (2013.01); *G06F 3/012* (2013.01); *G06F 3/015* (2013.01); *G06F 3/017* (2013.01); *G06F 3/038* (2013.01); *G06F 3/0346* (2013.01); *G06F 3/16* (2013.01); *G10L 15/22* (2013.01); *A61B 2560/0487* (2013.01); *G06K 9/00335* (2013.01); *G10L 2015/223* (2013.01)

(56) References Cited

U.S. PATENT DOCUMENTS

| | | |
|---|---|---|
| 2007/0239005 A1 | 10/2007 | Ogasawara |
| 2013/0147686 A1 | 6/2013 | Clavin et al. |
| 2013/0288596 A1* | 10/2013 | Suzuki .................... B63C 11/26 455/40 |
| 2014/0039827 A1 | 2/2014 | Yuzawa |
| 2014/0300532 A1 | 10/2014 | Karkkainen et al. |
| 2015/0104044 A1 | 4/2015 | Lee et al. |
| 2015/0185855 A1* | 7/2015 | Elak ...................... G06F 3/0487 345/156 |
| 2015/0342442 A1* | 12/2015 | Tadano .............. A61B 1/00149 600/102 |
| 2015/0355805 A1* | 12/2015 | Chandler .............. G06F 3/0482 715/784 |
| 2017/0038838 A1* | 2/2017 | Kato ........................ G06F 3/01 |
| 2017/0039750 A1* | 2/2017 | Tong ...................... G06T 13/40 |
| 2018/0239424 A1* | 8/2018 | Nishihashi .............. B60R 16/02 |

FOREIGN PATENT DOCUMENTS

| | | |
|---|---|---|
| JP | 2000-163196 A | 6/2000 |
| JP | 2001-100903 A | 4/2001 |
| JP | 2001-299691 A | 10/2001 |
| JP | 2007-195892 A | 8/2007 |
| JP | 2008-046802 A | 2/2008 |
| JP | 2009-251658 A | 10/2009 |
| JP | 2014-126997 A | 7/2014 |

OTHER PUBLICATIONS

International Search Report; issued in PCT/JP2016/070073; dated Aug. 23, 2016.
Written Opinion; issued in PCT/JP2016/070073; dated Aug. 23, 2016.
International Preliminary Report on Patentability; issued in PCT/JP2016/070073; dated Mar. 6, 2018.

* cited by examiner

FIG. 11
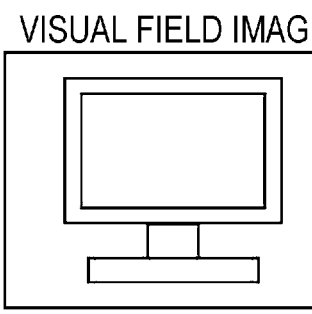
VISUAL FIELD IMAGE
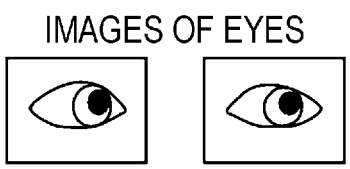
IMAGES OF EYES
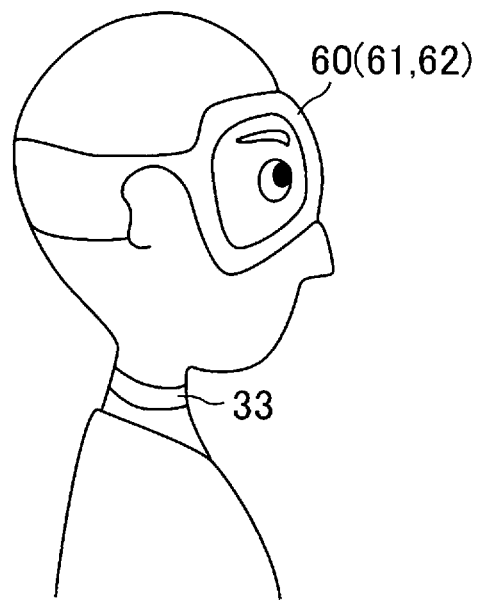

APPARATUS OPERATION DEVICE, APPARATUS OPERATION METHOD, AND ELECTRONIC APPARATUS SYSTEM

CROSS-REFERENCE TO RELATED APPLICATIONS

This application is a Continuation of PCT International Application No. PCT/JP2016/070073 filed on Jul. 7, 2016, which claims priority under 35 U.S.C § 119(a) to Japanese Patent Application No. 2015-174575 filed on Sep. 4, 2015. Each of the above application(s) is hereby expressly incorporated by reference, in its entirety, into the present application.

BACKGROUND OF THE INVENTION

1. Field of the Invention

The present invention relates to an apparatus operation device, an apparatus operation method, and an electronic apparatus system, and particularly relates to a technique for operating an apparatus by using a line of sight and a motion of the neck of a user.

2. Description of the Related Art

Various types of apparatuses are typically operated by a user with his/her hand or foot. However, depending on a type or usage situation of an apparatus, restrictions may be imposed on a user's action or the arrangement of the apparatus or an operation device. For example, in an operation of a mobile apparatus, such as a smartphone or game machine, driving of a car, or an operation of a medical apparatus, a user may be unable to freely use both hands. As for a medical apparatus, the user may need to peel off/put on gloves or wash hands before/after operating the apparatus. That is, in operation techniques using a hand or foot, it may be difficult to smoothly perform an operation.

As operation techniques not using a hand or foot, operation techniques using a line of sight and a gesture are known (see, for example, JP2014-126997A, JP2000-163196A, JP2001-100903A, and JP2007-195892A).

JP2014-126997A and JP2000-163196A describe that a point of gaze of a user is detected based on a captured image of the head of the user, a predetermined action of the head (for example, a nod action of shaking the head vertically) is detected based on the captured image of the head of the user, and an operation corresponding to the point of gaze of the user is decided on upon the predetermined action of the head being detected.

JP2001-100903A describes that an action of a hand of a user is detected based on a captured image of the hand of the user, and a process of moving a cursor to a line-of-sight position is started (turn on a cursor following mode) if one finger is raised, whereas the process of moving the cursor to the line-of-sight position is finished (turn off the cursor following mode) if no finger is raised but a first is made.

JP2007-195892A describes that a line-of-sight position is calculated based on an image captured by a camera of a unit that can be mounted on the head of a user (line-of-sight position input unit) and a focus position is moved to the line-of-sight position. JP2007-195892A also describes that a magnetic sensor for detecting a position and an angle of the head of the user is used.

In addition, an operation technique using a voice input is known. JP2001-299691A describes that, if a user presses a foot switch and inputs a name (for example, "decrease light intensity") of an icon (for example, a "decrease light intensity" icon) by voice while gazing at the icon displayed on a display unit for a predetermined period of time or more, the operation of the user is decided on and an action corresponding to the icon is performed. The voice input is performed by using a pin microphone that is attached to clothes or a head microphone that is mounted on the head.

SUMMARY OF THE INVENTION

However, there has not been provided an operation technique that enables a user to easily perform an operation even if both hands are occupied and that enables an operation intended by the user to be appropriately detected and performed.

In the techniques described in JP2014-126997A and JP2000-163196A, an operation determined based on detection of a line of sight is decided on upon a predetermined action of the head of a user being detected, and thus the effect of avoiding a malfunction can be more expected than in the case of only performing determination based on detection of a line of sight. However, since an action of the head of the user is recognized based on an image that is obtained by photographing the head, it is difficult for the apparatus to appropriately determine whether the motion of the head results from a motion of neck muscles according to the user's intention or results from an unconscious motion of the body. If it is assumed that a determination process is modified to a determination process in which a small motion or a simple motion performed by a user is ignored by the apparatus and in which only a large motion (for example, a motion of tilting the head by 45 degrees or more) or a complicated motion performed by the user is regarded as effective, the user is forced to perform a large motion or a complicated motion. Accordingly, it is impossible to perform a smooth operation although a malfunction can be avoided. In addition, the user will get tired.

Also in the techniques described in JP2001-100903A, JP2007-195892A, and JP2001-299691A, it is not possible to achieve both an easy operation under a situation where both hands of a user are occupied and appropriate detection and execution of an operation intended by the user.

On the other hand, under circumstances where there is an issue of medical errors, recording of conversation between medical doctors may be considered to determine the propriety of surgery. However, music is played during surgery in a surgery room and a plurality of people is involved in the surgery. Thus, in the voice input according to JP2001-299691, ambient music and voice are recorded, and it is not possible to accurately record the situation of the surgery.

The present invention has been made in view of the above-described circumstances, and an object of the present invention is to provide an apparatus operation device, an apparatus operation method, and an electronic apparatus system that enable a user to easily perform an operation even if both hands are occupied and that enable an operation intended by the user to be appropriately detected and performed.

To achieve the above-described object, an apparatus operation device according to a first aspect of the present invention includes a line-of-sight detecting unit that detects a line of sight of a user; a neck-mounted terminal that is mounted around a neck of the user and detects a motion of the neck of the user; a determining unit that determines, based on the line of sight that has been detected and the motion of the neck that has been detected, at least one of a target apparatus to be operated or operation details for the target apparatus; and a control unit that controls the target apparatus in accordance with the determination.

According to this aspect, an operation can be easily performed even if both hands of a user are occupied, and an operation intended by the user can be appropriately detected and performed.

In an apparatus operation device according to a second aspect of the present invention, the determining unit determines, based on the line of sight that has been detected, at least one of the target apparatus or the operation details, and confirms the determination, based on the motion of the neck that has been detected.

In an apparatus operation device according to a third aspect of the present invention, the line-of-sight detecting unit detects a movement of the line of sight, and the determining unit determines, based on the movement of the line of sight that has been detected, at least one of the target apparatus or the operation details.

In an apparatus operation device according to a fourth aspect of the present invention, the operation details include a function that the control unit causes the target apparatus to execute, and an execution condition for the function.

In an apparatus operation device according to a fifth aspect of the present invention, the apparatus operation device includes a voice recognizing unit that recognizes a voice of the user by using a vibration of a throat of the user, the vibration being detected by the neck-mounted terminal.

In an apparatus operation device according to a sixth aspect of the present invention, the apparatus operation device includes a voice recording unit that records the voice that has been recognized.

In an apparatus operation device according to a seventh aspect of the present invention, the line-of-sight detecting unit suspends detection of the line of sight upon detection of the motion of the neck being started by the neck-mounted terminal, and starts the detection of the line of sight upon the detection of the motion of the neck being finished by the neck-mounted terminal.

In an apparatus operation device according to an eighth aspect of the present invention, the determining unit invalidates detection of the line of sight if the motion of the neck that has been detected is larger than a threshold.

To achieve the above-described object, an apparatus operation method according to the present invention is an apparatus operation method for an apparatus operation device including a line-of-sight detecting unit that detects a line of sight of a user and a neck-mounted terminal that is mounted around a neck of the user and detects a motion of the neck of the user, the apparatus operation method including a determination step of determining, based on the line of sight that has been detected and the motion of the neck that has been detected, at least one of a target apparatus to be operated or operation details for the target apparatus; and a control step of controlling the target apparatus in accordance with the determination.

To achieve the above-described object, an electronic apparatus system according to the present invention includes the apparatus operation device and an electronic apparatus which is the target apparatus.

The electronic apparatus is a medical apparatus, for example.

According to the present invention, an operation can be easily performed even if both hands of a user are occupied, and an operation intended by the user can be appropriately detected and performed.

BRIEF DESCRIPTION OF THE DRAWINGS

FIG. 11 is an explanatory diagram for describing a visual field image and images of eyes that are captured by a head-mounted terminal in the apparatus operation device according to the second embodiment;

DESCRIPTION OF THE PREFERRED EMBODIMENTS

Hereinafter, embodiments of an apparatus operation device, an apparatus operation method, and an electronic apparatus system according to the present invention will be described with reference to the attached drawings.

First Embodiment

Figure 1:
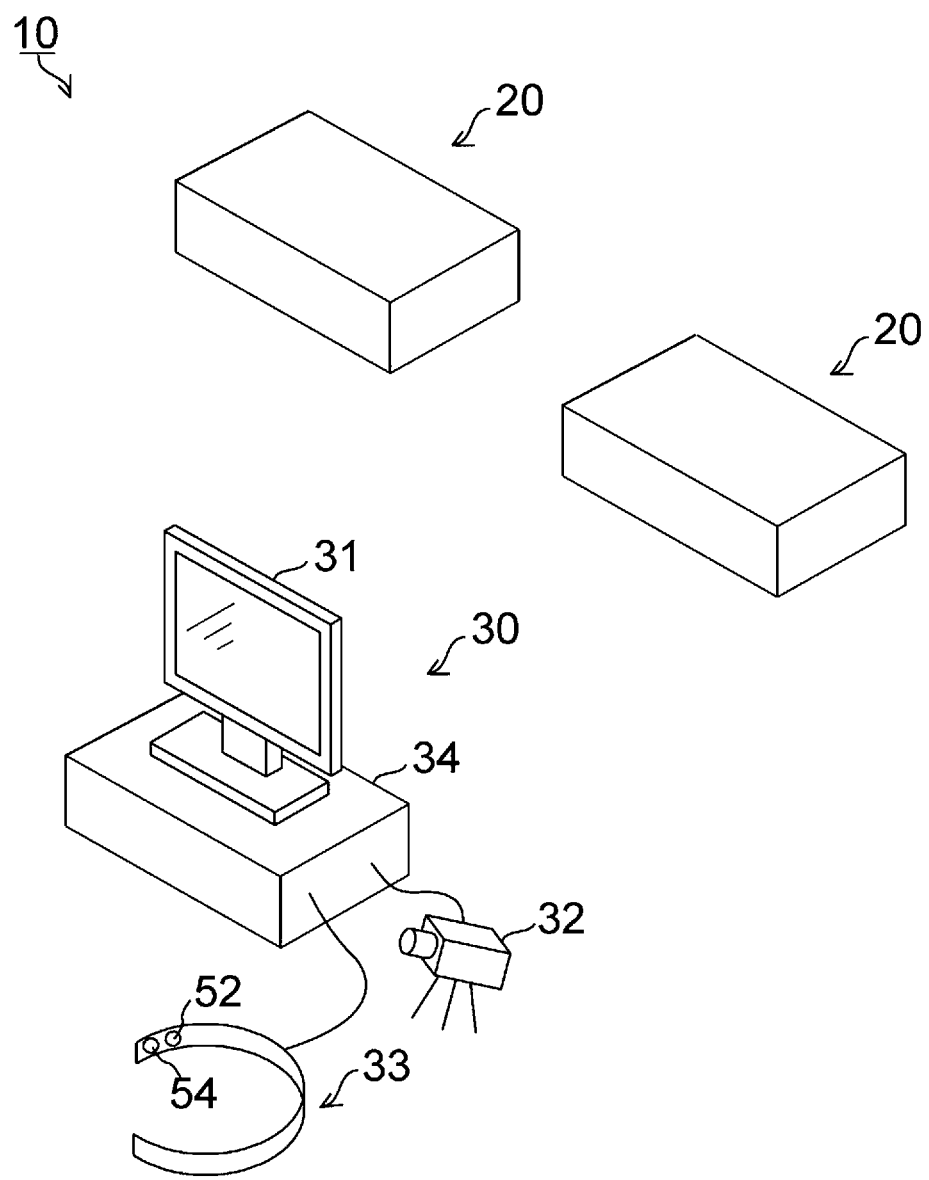
FIG. 1 is a diagram illustrating the overall configuration of an example of an electronic apparatus system according to a first embodiment.
Figure 2:
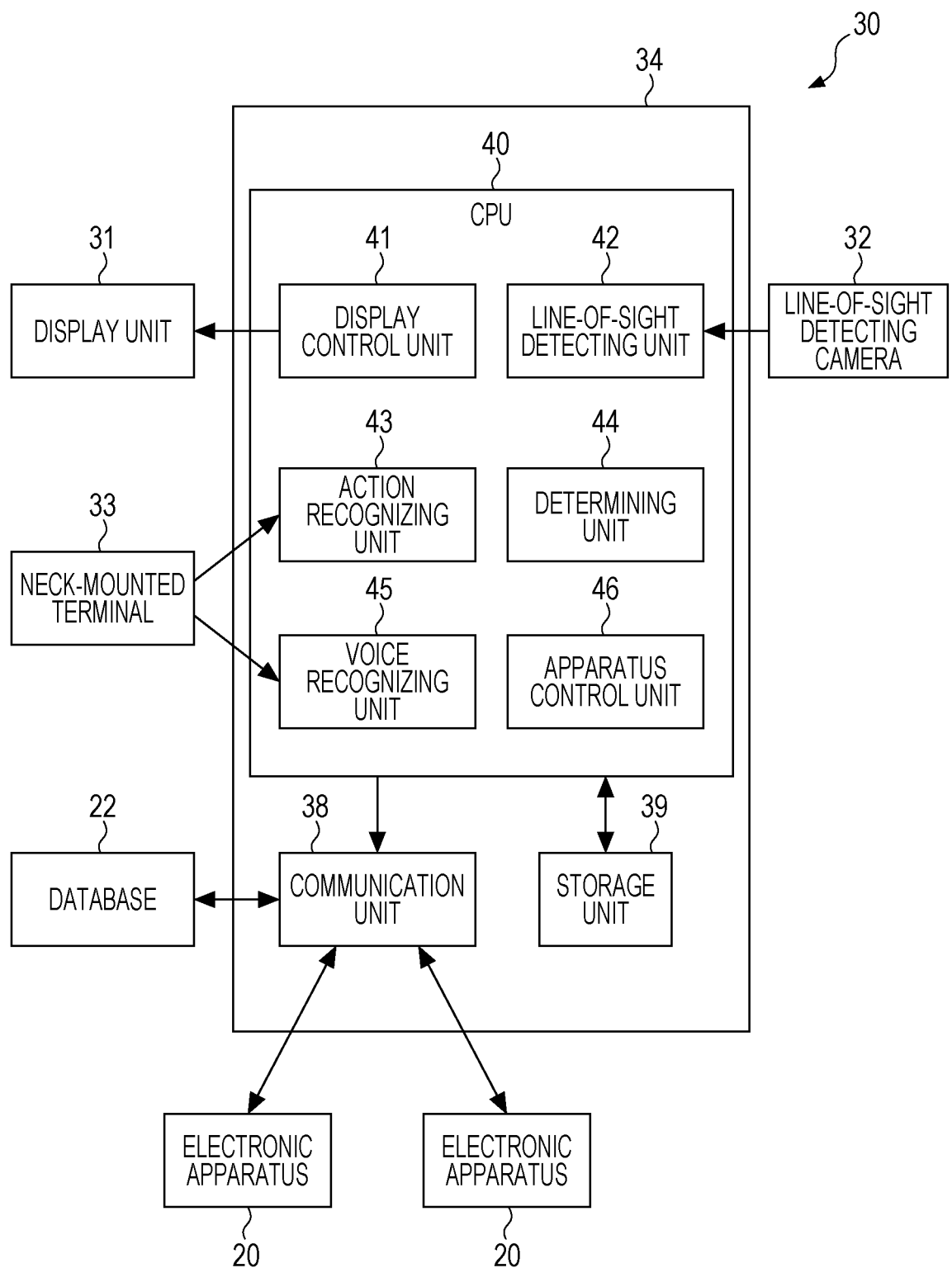
FIG. 2 is a block diagram illustrating an example of an apparatus operation device according to the first embodiment.

FIG. 1 is a diagram illustrating the overall configuration of an example of an electronic apparatus system according to a first embodiment of the present invention, and FIG. 2 is a block diagram illustrating an example of an apparatus operation device according to the first embodiment of the present invention.

As illustrated in FIG. 1, an electronic apparatus system 10 includes electronic apparatuses 20, each of which is a target apparatus to be operated, and an apparatus operation device 30 that controls the electronic apparatuses 20.

The apparatus operation device 30 includes a display unit 31 (also referred to as a "display") that performs display for a user, a line-of-sight detecting camera 32 that captures an image of the face of the user to detect a line of sight of the user, a neck-mounted terminal 33 that is mounted around the neck of the user and detects a motion of the neck of the user, and an arithmetic unit 34 that serves as a main body unit, which controls the display unit 31, the line-of-sight detecting camera 32, and the neck-mounted terminal 33, and that performs various arithmetic operations.

The display unit 31 is constituted by a display device, such as a liquid crystal display device.

The line-of-sight detecting camera 32 is located near the display unit 31, captures an image of at least an eye of the user to generate an image (hereinafter referred to as a "user image") including the image of the eye, and outputs the generated image. In the case of extracting only the portion of an eye in the face of the user, the extraction may be performed by using a function of the line-of-sight detecting camera 32, or a function of the extraction may be provided in the arithmetic unit 34. To detect a line of sight reliably and stably, a plurality of line-of-sight detecting cameras 32 may be provided.

The neck-mounted terminal 33 is a terminal that is to be mounted around the neck of the user and includes, as illustrated in FIG. 1, a neck motion sensor 52 that detects a motion of the neck of the user and a vibration sensor 54 that detects a vibration of the throat of the user on the neck.

As the neck motion sensor 52, a sensor device, such as a myoelectric sensor that detects a motion of a neck muscle, a distortion sensor, or an acceleration sensor, is used. A sensor device other than these sensors may be used. As "a motion of the neck", any of a motion of a neck muscle, a motion of a neck bone, or a motion of a neck surface (i.e., a motion of a neck skin) may be detected by the neck motion sensor 52. A plurality of types of sensor devices may be used to perform detection.

As the vibration sensor 54, an acceleration sensor that detects a vibration of a neck bone is used, for example. Another type of sensor may be used.

A single sensor device may be implemented as the neck motion sensor 52 and the vibration sensor 54, and the single sensor device may be caused to detect a motion of the neck and a vibration of the throat. For example, a single acceleration sensor is implemented as the neck motion sensor 52 and the vibration sensor 54, a low-frequency component is extracted from an output signal of the acceleration sensor to generate a signal representing a motion of the neck, and a high-frequency component is extracted from the output signal to generate a signal representing a vibration of the throat.

As illustrated in FIG. 2, the arithmetic unit 34 includes a communication unit 38 that communicates with the plurality of electronic apparatuses 20, a storage unit 39 that stores a program for controlling the operation of the electronic apparatuses 20 and information that is necessary to execute the program, and a central processing unit (CPU) 40 that controls the individual units of the apparatus operation device 30 by executing the program stored in the storage unit 39.

The communication unit 38 is constituted by a communication device that communicates with the electronic apparatuses 20. FIG. 1 illustrates a case where the communication unit 38 communicates with the electronic apparatuses 20 in a wireless manner, but the communication unit 38 may communicate with the electronic apparatuses 20 in a wired manner through a local area network or the like. In addition, the communication unit 38 may communicate with a device outside the arithmetic unit 34 (for example, a database 22), which is not illustrated in FIG. 1, through a local area network or the like.

The storage unit 39 includes a nonvolatile storage device that stores programs and the like and a readable/writable storage device that is used as a working area of the programs.

The CPU 40 includes, as illustrated in FIG. 2, a display control unit 41 that performs display control for the display unit 31; a line-of-sight detecting unit 42 that detects, based on a user image output from the line-of-sight detecting camera 32, a line of sight of a user; an action recognizing unit 43 that recognizes, based on a motion of the neck of the user that has been detected by the neck motion sensor 52 of the neck-mounted terminal 33, an action of the head of the user; a determining unit 44 that determines, based on the line of sight detected by the line-of-sight detecting unit 42 and the action of the head of the user that has been recognized based on the motion of the neck of the user, at least one of a target apparatus to be operated or operation details for the target apparatus; a voice recognizing unit 45 that recognizes a voice of the user by using a vibration of the throat of the user detected at the neck of the user by the vibration sensor 54 of the neck-mounted terminal 33; and an apparatus control unit 46 that controls the electronic apparatuses 20 in accordance with the determination made by the determining unit 44.

The display control unit 41 has a function of causing the display unit 31 to display screen information that is necessary for a user operation.

Figure 3:
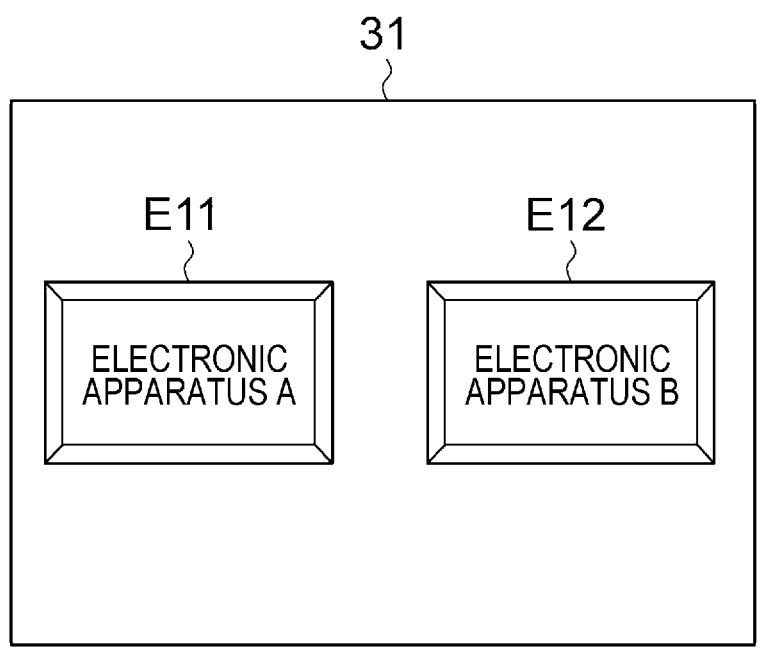
FIG. 3 is a diagram illustrating an example of screen information for designating a target apparatus to be operated.

As illustrated in FIG. 3, the display control unit 41 causes the display unit 31 to display screen information (hereinafter referred to as "target apparatus designation screen information") that allows a user to designate, by a line-of-sight input, an icon (for example, an icon E11) representing a target apparatus to be operated (for example, "electronic apparatus A") among a plurality of icons E11 and E12 respectively representing the plurality of electronic apparatuses 20 (for example, "electronic apparatus A" and "electronic apparatus B").

Figure 4A:
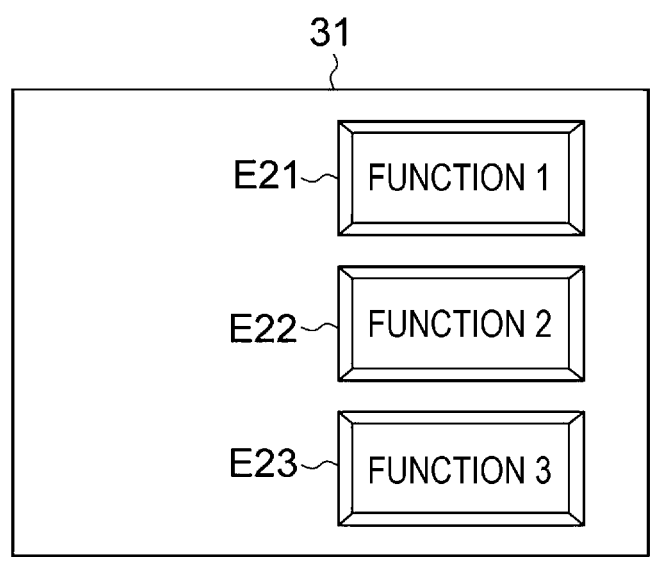
FIGS. 4A and 4B are diagrams illustrating examples of screen information for designating operation details.

Also, as illustrated in FIG. 4A, the display control unit 41 causes the display unit 31 to display screen information (hereinafter referred to as "function designation screen information") that allows a user to designate, by a line-of-sight input, an icon (for example, an icon E21) representing a function to be executed by a target apparatus to be operated (for example, "function 1") among a plurality of icons E21, E22, and E23 respectively representing a plurality of functions (for example, "function 1", "function 2", and "function 3").

Figure 4B:
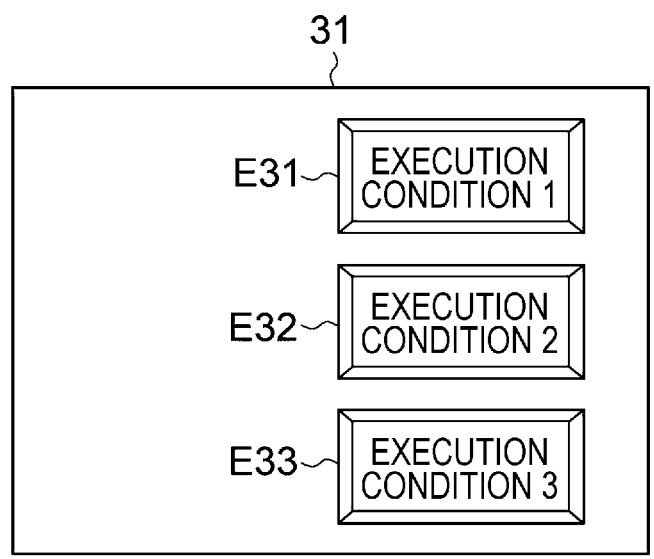

Also, as illustrated in FIG. 4B, the display control unit 41 causes the display unit 31 to display screen information (hereinafter referred to as "execution condition designation screen information") that allows a user to designate, by a line-of-sight input, an icon (for example, an icon E31) representing an execution condition for a function to be executed by a target apparatus to be operated among a plurality of icons E31, E32, and E33 respectively representing a plurality of execution conditions (for example, "execution condition 1", "execution condition 2", and "execution condition 3").

"Function designation screen information" and "execution condition designation screen information" are examples of screen information that allows a user to designate, by a line-of-sight input, icons representing operation details (hereinafter referred to as "operation details designation screen information"). That is, "operation details" in this example include "function" and "execution condition".

Next, line-of-sight detection performed by the line-of-sight detecting unit 42 will be described.

A line of sight (point of gaze) can be detected from an image of an eye of the user, based on the position of the iris, which is a movable point (a portion that moves relative to a reference point), relative to the inner corner of the eye, which is a reference point. For example, in a case where the iris of the left eye is far from the inner corner of the left eye, the user is looking left. On the other hand, in a case where the iris of the left eye is close to the inner corner of the left eye, the user is looking right.

A line of sight can also be detected based on the position of the pupil, which is a movable point, relative to the position of the corneal reflection, which is a reference point. For example, in a case where the pupil of the left eye is closer than the corneal reflection to the outer corner side of the left eye, the user is looking left. In a case where the pupil of the left eye is closer than the corneal reflection to the inner corner side of the left eye, the user is looking right. In the case of using this method, the face of the user is irradiated with infrared rays and photographed by an infrared camera.

The line-of-sight detecting unit 42 of this example detects a movement of a line of sight (i.e., continuously detects a line of sight), and the determining unit 44 of this example determines, based on the movement of the line of sight that has been detected, a target apparatus to be operated and operation details for the target apparatus. The determining unit 44 may determine, based on the movement of the line of sight that has been detected, at least one of a target apparatus to be operated or operation details.

Next, a specific example of action recognition by the action recognizing unit 43 will be described.

Figure 5A:
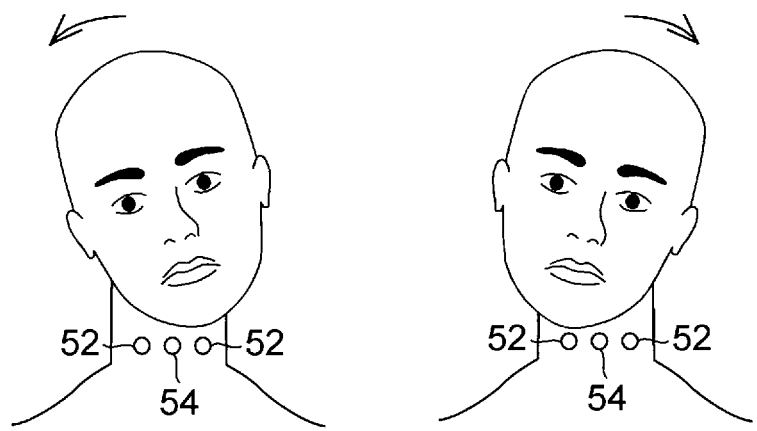
FIGS. 5A to 5C are explanatory diagrams for describing detection of a motion of a neck.
Figure 5B:
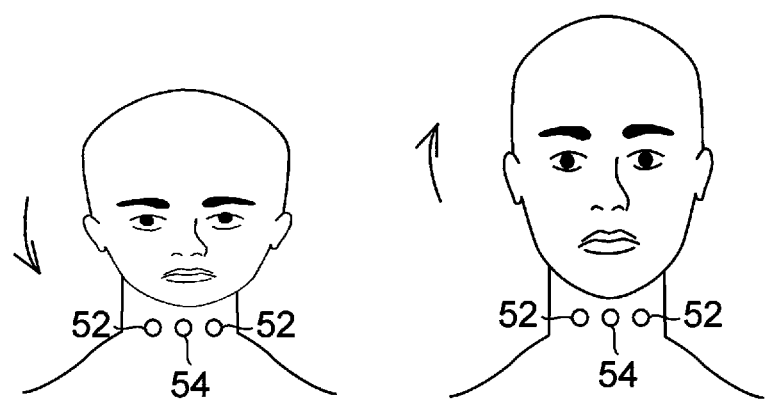
Figure 5C:
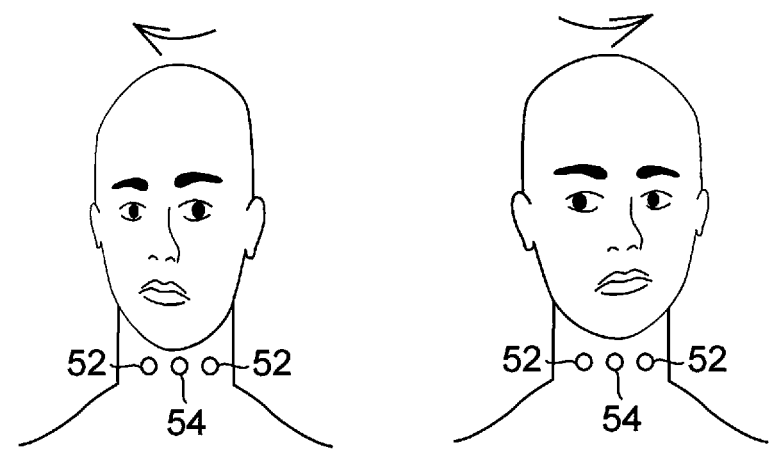

Examples of an action that is recognized by the action recognizing unit 43 include "head tilt" (an action of tilting the head) illustrated in FIG. 5A, "nod" (an action of shaking the head vertically) illustrated in FIG. 5B, and "head shake" (an action of shaking the head horizontally) illustrated in FIG. 5C. That is, in response to an instruction from the brain of the user who intends to perform an action, such as "head tilt", "nod", or "head shake", muscles of the neck are moved and accordingly the head is moved. Action recognition is performed by directly detecting "a motion of the neck" by the neck motion sensor 52 of the neck-mounted terminal 33, not by detecting "a motion of the head", which is a result of a motion of the neck. Therefore, the action recognizing unit 43 is capable of appropriately recognizing an action intended by the user.

The determining unit 44 determines, based on the line of sight detected by the line-of-sight detecting unit 42, at least one of a target apparatus to be operated or operation details, and confirms the determination, based on the motion of the neck detected by the neck-motion sensor 52 of the neck-mounted terminal 33. The determining unit 44 of this example makes a determination based on an action recognized by the action recognizing unit 43 by using a detection result obtained by the neck motion sensor 52. Such a case is also included in the concept of "to make a determination based on a motion of the neck" or "to confirm the determination based on a motion of the neck" in the present invention.

The voice recognizing unit 45 recognizes a voice of the user, based on a vibration of the throat of the user detected at the neck of the user by the vibration sensor 54 of the neck-mounted terminal 33.

The apparatus control unit 46 is an example of a "control unit" according to the present invention and controls, in accordance with a determination made by the determining unit 44, an electronic apparatus 20 which is a target apparatus to be operated.

For example, if the determining unit 44 determines that "electronic apparatus A" has been designated from the target apparatus designation screen information illustrated in FIG. 3, determines that "function 1" has been designated from the function designation screen information illustrated in FIG. 4A, and determines that "execution condition 1" has been designated from the execution condition designation screen information illustrated in FIG. 4B, the communication unit 38 transmits an instruction to execute function 1 under execution condition 1 to electronic apparatus A which is a target apparatus to be operated.

Figure 6:
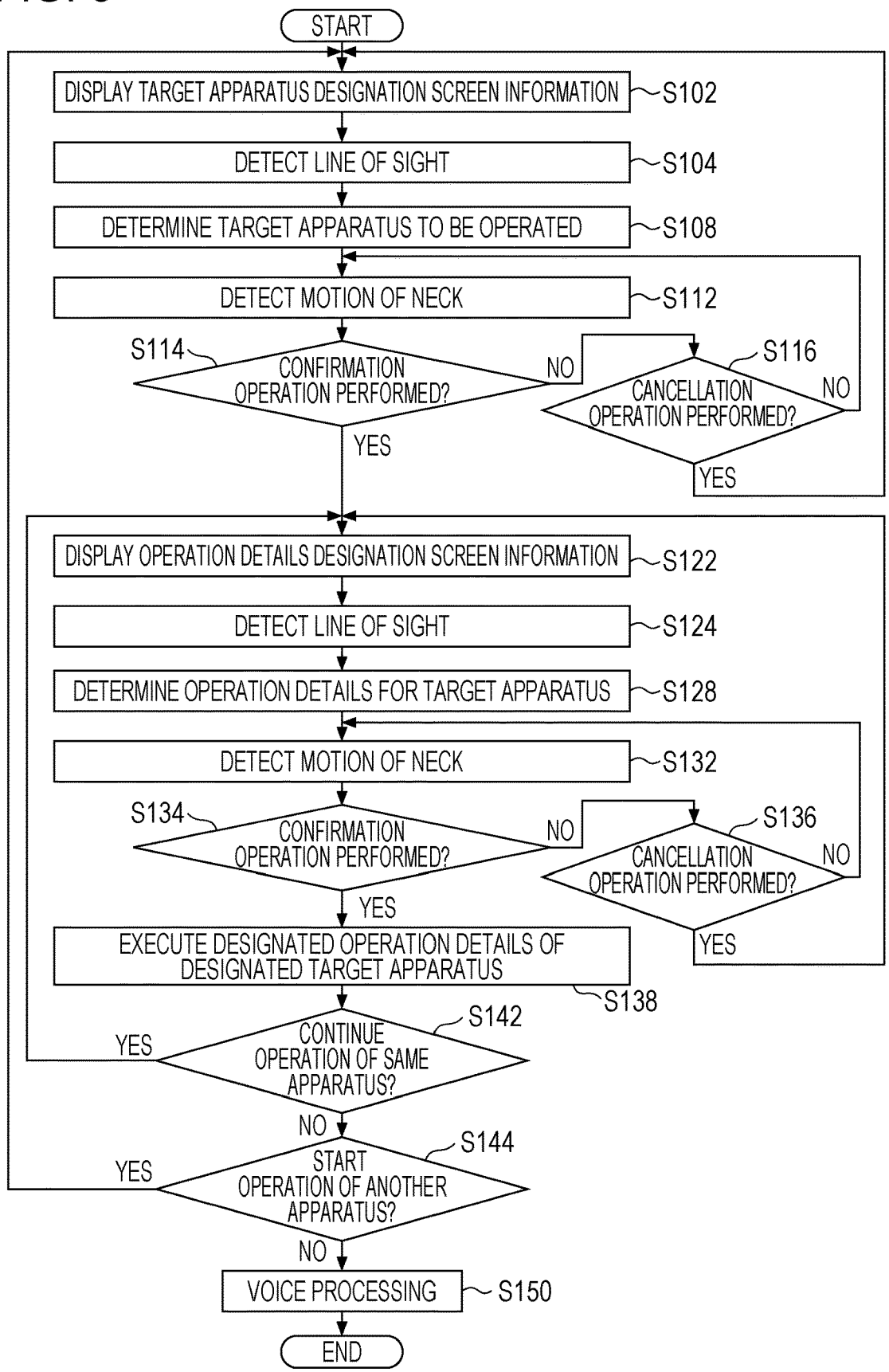
FIG. 6 is a flowchart illustrating a flow of a process of a first example of an apparatus operation method using the apparatus operation device according to the first embodiment.

FIG. 6 is a flowchart illustrating a flow of a process of a first example of an apparatus operation method using the apparatus operation device 30 of this embodiment. The process is executed by the CPU 40 in accordance with a program stored in advance in the storage unit 39.

Upon the process being started, in step S102, the display control unit 41 causes the display unit 31 to display the target apparatus designation screen information, as illustrated in FIG. 3.

Figure 7:
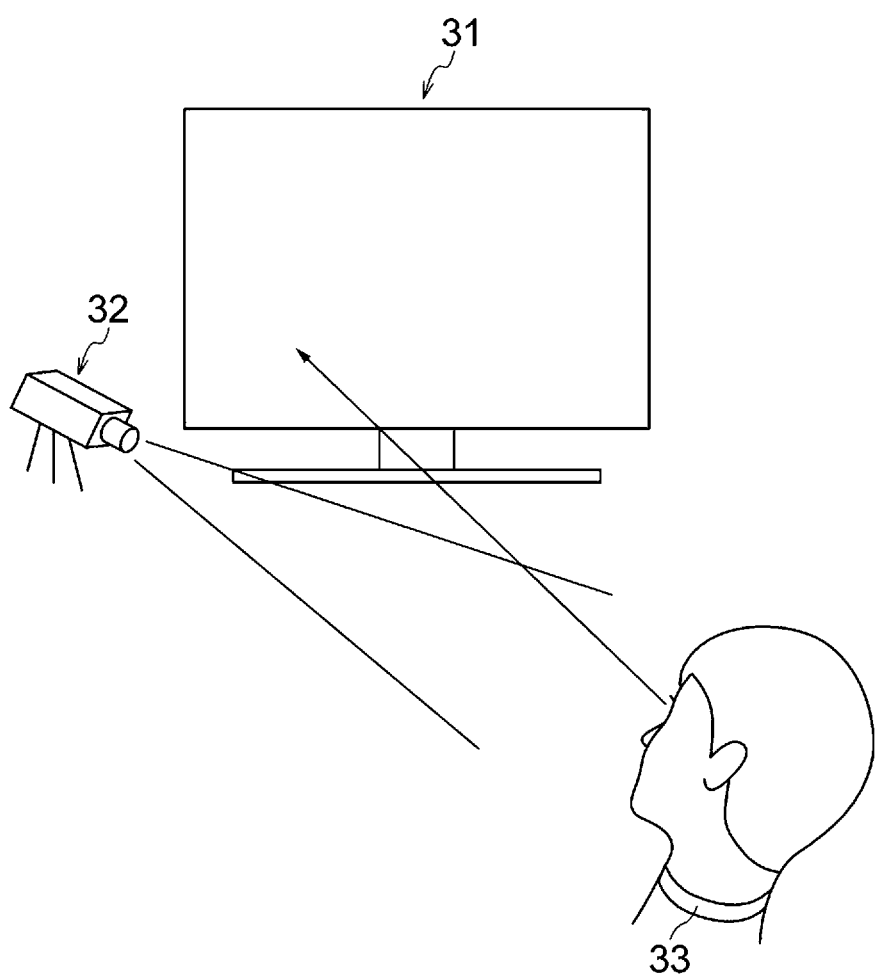
FIG. 7 is an explanatory diagram for describing detection of a line of sight in the apparatus operation device according to the first embodiment.

Subsequently, the process proceeds to step S104, where the line-of-sight detecting unit 42 detects a line of sight of a user. For example, if the line of sight of the user is directed on the screen of the display unit 31, as illustrated in FIG. 7, a position at which the line of sight of the user is directed (a line-of-sight position) on the screen of the display unit 31 is calculated based on an image (user image) captured by the line-of-sight detecting camera 32.

Subsequently, the process proceeds to step S108, where the determining unit 44 determines, based on the line of sight detected in step S104, a target apparatus to be operated that has been designated by the user by using the line of sight.

Subsequently, the process proceeds to step S112, where the neck motion sensor 52 of the neck-mounted terminal 33 detects a motion of the neck of the user and the action recognizing unit 43 recognizes an action of the user.

Subsequently, the process proceeds to step S114, where the determining unit 44 determines whether or not the user has performed an action of a confirmation operation (for example, "nod" illustrated in FIG. 5B).

If it is determined that a confirmation operation has not been performed (NO in step S114), the process proceeds to step S116, where the determining unit 44 determines whether or not the user has performed an action of a cancellation operation (for example, "head shake" illustrated in FIG. 5C). If it is determined that a cancellation operation has been performed (YES in step S116), the determination result about the target apparatus to be operated that is based on the line-of-sight detection result is cleared, and the process returns to step S102. If it is determined that a cancellation operation has not been performed (NO in step S116), the process returns to step S112, where detection of a motion of the neck (step S112) and determination of a confirmation operation (step S114) are repeated.

If it is determined that a confirmation operation has been performed (YES in step S114), the process proceeds to step S122, where the display control unit 41 causes the display unit 31 to display the operation details designation screen information, as illustrated in FIGS. 4A and 4B. For example, the "function designation screen information" illustrated in FIG. 4A, the "execution condition designation screen information" illustrated in FIG. 4B, or screen information including both the pieces of screen information is displayed as the operation details designation screen information.

Subsequently, the process proceeds to step S124, where the line-of-sight detecting unit 42 detects a line of sight of the user. That is, the line-of-sight detecting unit 42 calculates, based on an image (user image) captured by the line-of-sight detecting camera 32, a position at which the line of sight of the user is directed (line-of-sight position) on the screen of the display unit 31.

Subsequently, the process proceeds to step S128, where the determining unit 44 determines, based on the line of sight detected in step S124, operation details designated by the user by using the line of sight. That is, the determining unit 44 determines operation details for the electronic apparatus 20 as a target to be operated.

Subsequently, the process proceeds to step S132, where the neck motion sensor 52 of the neck-mounted terminal 33 detects a motion of the neck of the user and the action recognizing unit 43 recognizes an action of the user.

Subsequently, the process proceeds to step S134, where the determining unit 44 determines whether or not the user has performed an action of a confirmation operation (for example, "nod" illustrated in FIG. 5B).

If it is determined that a confirmation operation has not been performed (NO in step S134), the process proceeds to step S136, where the determining unit 44 determines whether or not the user has performed an action of a cancellation operation (for example, "head shake" illustrated in FIG. 5C). If it is determined that a cancellation operation has been performed (YES in step S136), the determination result about the operation details that is based on the line-of-sight detection result is cleared, and the process returns to step S122. If it is determined that a cancellation operation has not been performed (NO in step S136), the process returns to step S132, where detection of a motion of the neck (step S132) and determination of a confirmation operation (step S134) are repeated.

If it is determined that a confirmation operation has been performed (YES in step S134), the process proceeds to step S138, where the designated function of the designated target apparatus to be operated is executed in accordance with the designated operation details.

Subsequently, the process proceeds to step S142, where it is determined whether or not to continue an operation of the same electronic apparatus 20 among the plurality of electronic apparatuses 20. In the case of continuing an operation of the same electronic apparatus 20 (YES in step S142), the process returns to step S122. In step S144, it is determined whether or not to start an operation of another electronic apparatus 20. In the case of starting an operation of another electronic apparatus 20 (YES in step S144), the process returns to step S102.

In the case of finishing the operation of the same and another electronic apparatus 20 (NO in step S144), the process proceeds to step S150, where voice processing is executed to generate and output a report.

The details of the voice processing in step S150 will be described. First, the vibration sensor 54 of the neck-mounted terminal 33 detects a vibration of the throat at the neck of the user. Subsequently, the voice recognizing unit 45 recognizes, based on the detected vibration of the throat of the user, a voice of the user. Subsequently, the recognized voice is recorded. That is, only the voice of the person who is wearing the neck-mounted terminal 33 can be easily recorded, without ambient music or sound being recorded.

Modes of recording a voice include a mode of performing recording inside the arithmetic unit 34, which is a main body unit of the apparatus operation device 30 (hereinafter referred to as an "inside recording mode"), and a mode of performing recording outside the arithmetic unit 34, which is a main body unit of the apparatus operation device 30 (hereinafter referred to as an "outside recording mode"), either of which may be used in the present invention. In the inside recording mode, voice data is recorded in, for example, the storage unit 39 under control of the CPU 40. In this example, the storage unit 39 is an example of a "voice recording unit". In the outside recording mode, voice data is output from the communication unit 38 (an example of a "voice data output unit") and is recorded in, for example, the database 22. In this example, the database 22 is an example of the "voice recording unit". For example, the voice data is written on a file and is transmitted to the database 22 through a local area network.

Although voice processing (step S150) is performed after the operation of the apparatus has been finished in FIG. 6, the present invention is not limited to such a case. Voices during the operation of the apparatus can be input, recognized, and recorded. For example, instructions and conversations of medical doctors and so forth during surgery can be recorded as voice data, which can be used as evidence if a medical accident occurs or can be used to pass on medical technologies.

After a report has been generated and output in the voice processing (step S150), the process ends.

In FIG. 6, steps S108, S114, S116, S128, S134, and S136 are an example of a "determination step" in the present invention. Step S138 is an example of a "control step" in the present invention.

In FIG. 6, line-of-sight detection by the line-of-sight detecting unit 42 and motion-of-neck detection by the neck-mounted terminal 33 are performed at different timings, but the line-of-sight detection and the motion-of-neck detection may be performed chronologically in parallel. In addition, each of the line-of-sight detection and the motion-of-neck detection may be performed continuously. In a case where such parallel control is performed, there is a possibility that the line-of-sight detection and the motion-of-neck detection are simultaneously performed. However, the line-of-sight detecting unit 42 in this example suspends detection of a line of sight upon detection of a motion of the neck being started by the neck-mounted terminal 33, and starts detection of a line of sight upon detection of a motion of the neck being finished by the neck-mounted terminal 33. For example, the line-of-sight detecting unit 42 suspends detection of a line of sight when detection of a motion of the neck is started in step S112 or step S132 in FIG. 6, and restarts detection of a line of sight when detection of a motion of the neck is finished.

Figure 8:
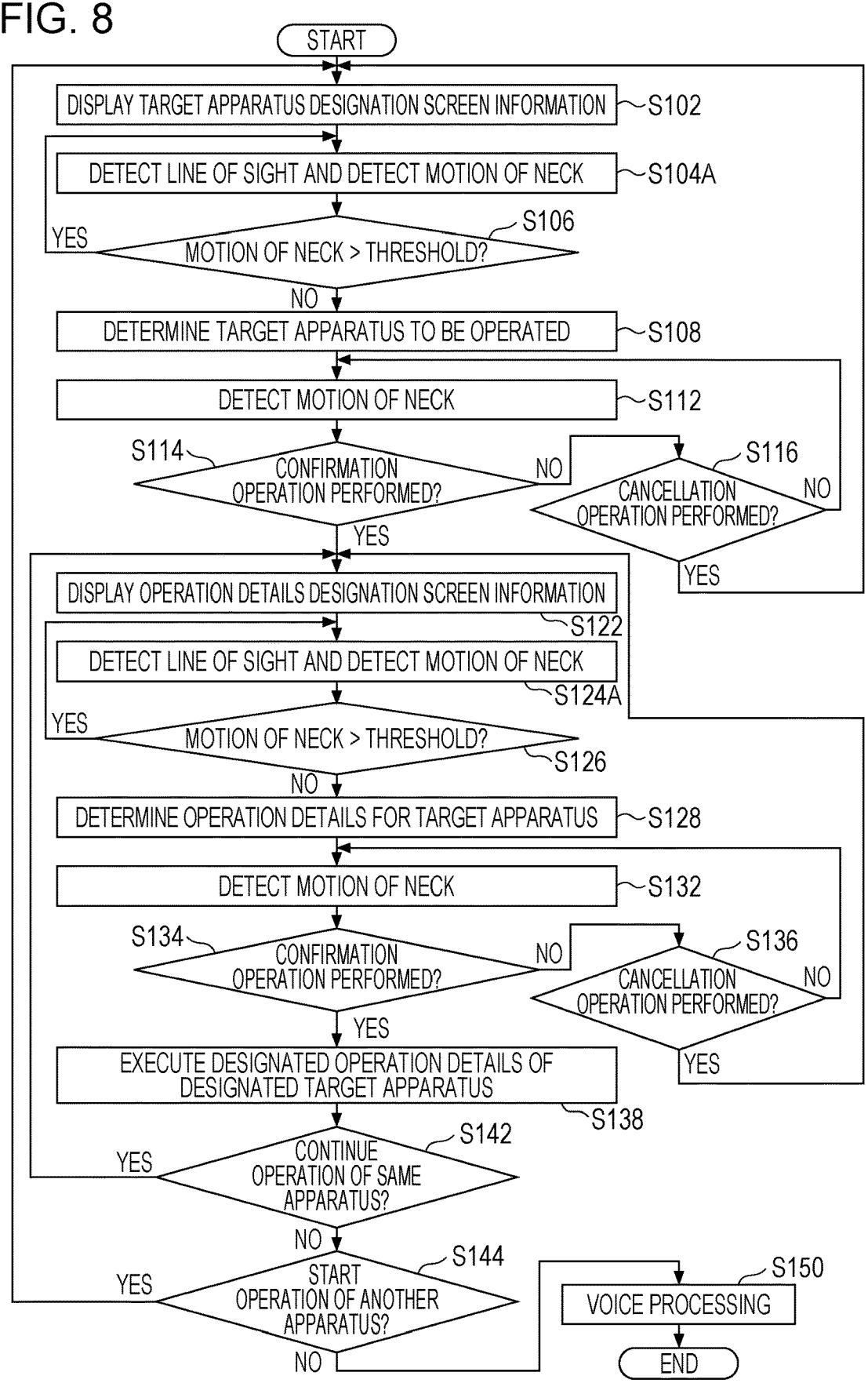
FIG. 8 is a flowchart illustrating a flow of a process of a second example of the apparatus operation method using the apparatus operation device according to the first embodiment.

FIG. 8 is a flowchart illustrating a flow of a process of a second example of the apparatus operation method using the apparatus operation device 30 of this embodiment. This process is executed by the CPU 40 in accordance with a program stored in advance in the storage unit 39. The same steps as those in the first example of this embodiment illustrated in FIG. 6 are denoted by the same numerals, and only different points will be described below.

In this example, line-of-sight detection and motion-of-neck detection (step S104A and step S124A) are performed instead of the line-of-sight detection (step S104 and step S124) illustrated in FIG. 6. After the line-of-sight detection and the motion-of-neck detection (step S104A and step S124A), the motion of the neck detected by the neck-mounted terminal 33 is compared with a threshold (step S106 and step S126). If the detected motion of the neck is larger than the threshold, the line-of-sight detection is invalidated.

That is, in this example, line-of-sight detection in a state where the neck of the user is stationary or slightly moving is validated, whereas line-of-sight detection in a state where the neck of the user is largely moving is invalidated. This is because, in a state where the neck of the user is largely moving, the head of the user is also largely moving, and as a result there is a possibility that the line of sight of the user will largely move in an unconscious way and that a determination not intended by the user will be made.

Here, examples of "a case where the detected motion of the neck is larger than the threshold" include a case where the amount of the detected motion of the neck (i.e., the magnitude of a movement vector) is larger than the threshold, a case where an evaluation value representing a fluctuation of the direction of the detected motion of the neck (i.e., the direction of a movement vector) is larger than the threshold, and so forth. That is, examples of the magnitude of the motion of the neck of the user that affects the accuracy of line-of-sight detection include the magnitude of fluctuation of the direction of a movement vector, as well as the magnitude of the movement vector. In other words, the "detected motion of the neck" conceptually includes an evaluation value of a movement vector as well as the magnitude of the movement vector.

Figure 9:
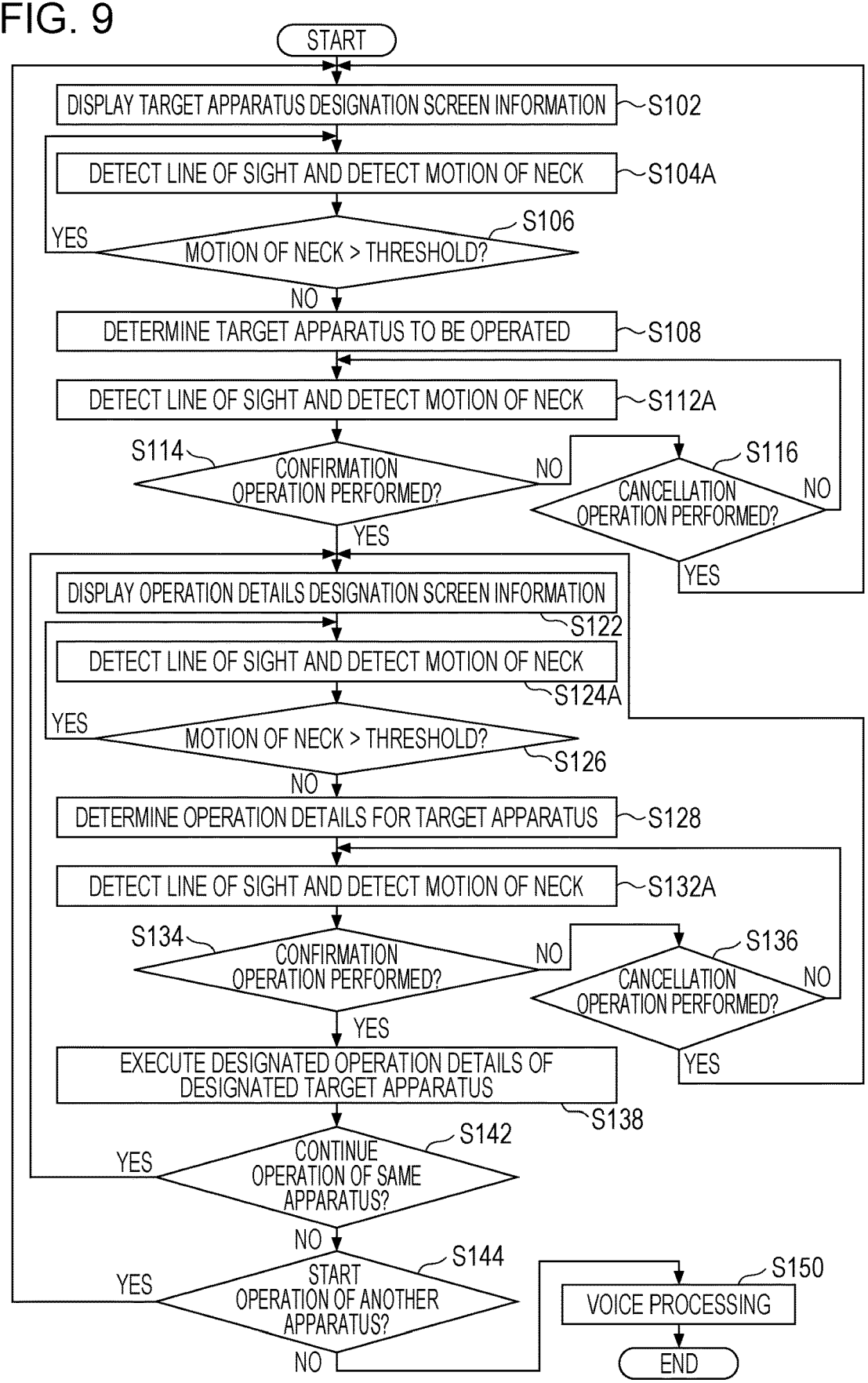
FIG. 9 is a flowchart illustrating a flow of a process of a third example of the apparatus operation method using the apparatus operation device according to the first embodiment.

FIG. 9 is a flowchart illustrating a flow of a process of a third example of the apparatus operation method using the apparatus operation device 30 of this embodiment. This process is executed by the CPU 40 in accordance with a program stored in advance in the storage unit 39. The same steps as those in the first example of this embodiment illustrated in FIG. 6 and those in the second example of this embodiment illustrated in FIG. 8 are denoted by the same numerals, and only different points will be described below.

In this example, line-of-sight detection and motion-of-neck detection (step S112A and step S132A) are performed instead of the motion-of-neck detection (step S112 and step S132) illustrated in FIGS. 6 and 8. Based on the results of the line-of-sight detection and the motion-of-neck detection (step S112A and step S132A), it is determined whether or not a confirmation operation has been performed (step S114 and step S134) and whether or not a cancellation operation has been performed (step S116 and step S136).

That is, in this example, it is determined based on not only a result of motion-of-neck detection but also a result of line-of-sight detection whether or not to confirm the determination of a target apparatus to be operated and operation details and whether or not to cancel the determination of the target apparatus to be performed and the operation details. This is because, if a determination of whether or not the user has performed a confirmation operation or a cancellation operation is made based on only a motion of the neck, a wrong determination that the user has performed a confirmation operation or a cancellation operation may be made if the user moves the neck in an unconscious way. As a method for avoiding such a wrong determination, a method for changing a determination criterion value, such as increasing a threshold to be compared with a detected motion of the neck, may be used. However, if the user is forced to make a larger motion of the neck, that is, to make a forced action, to avoid a wrong determination, the user is unable to perform a smooth operation, which may make the user tired.

Thus, a determination is made by using a characteristic that, if the user moves the neck while gazing at a graphical user interface (GUI) element (for example, a button) on the screen of the display unit 31, a line-of-sight position on the screen of the display unit 31 is substantially constant or within a range of slight movements regardless of a motion of the neck.

For example, in the case of determining whether or not the user has performed a confirmation operation by determining whether or not the user has performed a vertical head shake (nod), when the user shakes the head downward (or upward), the user's pupils move upward (or downward), so that it is detected that the magnitude of a movement vector of the neck becomes larger than a threshold for determining a motion of the neck, whereas it is detected that an amount of movement of a line-of-sight position on the screen becomes smaller than or equal to a threshold for determining a line-of-sight movement. In the case of determining whether or not the user has performed a cancellation operation by determining whether or not the user has performed a horizontal head shake, when the user shakes the head leftward (or rightward), the user's pupils move rightward (or leftward), so that it is detected that the magnitude of a movement vector of the neck becomes larger than a threshold for determining a motion of the neck, whereas it is detected that an amount of movement of a line-of-sight position on the screen becomes smaller than or equal to a threshold for determining a line-of-sight movement.

Second Embodiment

Figure 10:
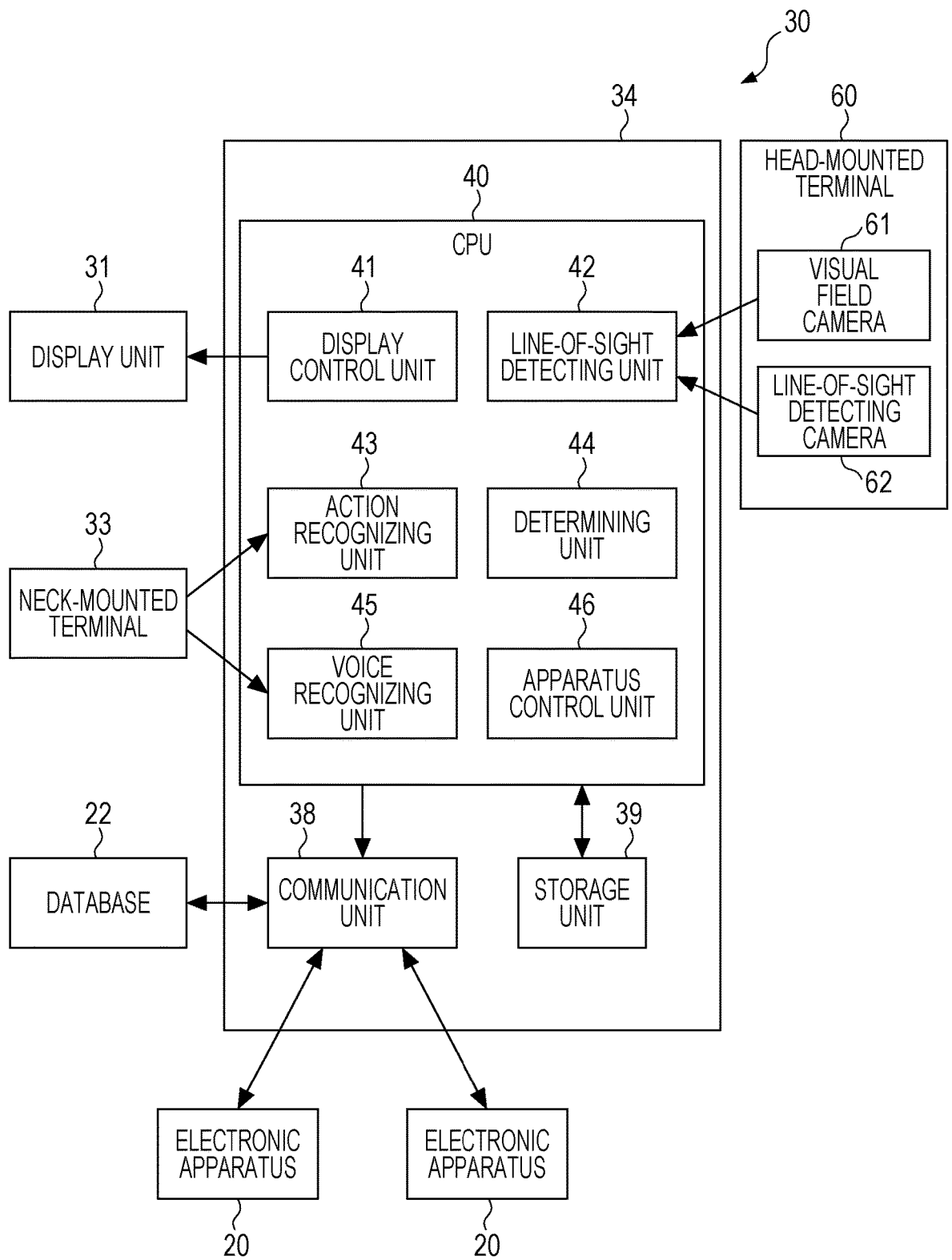
FIG. 10 is a block diagram illustrating an example of an apparatus operation device according to a second embodiment.

FIG. 10 is a block diagram illustrating an example of an apparatus operation device 30 according to a second embodiment. In FIG. 10, the same elements as those in the apparatus operation device 30 of the first embodiment illustrated in FIG. 2 are denoted by the same numerals, and only different points will be described below.

A head-mounted terminal 60 is a terminal that is to be mounted on the head of a user, as illustrated in FIG. 11, and includes a visual field camera 61 that captures an image of a photographic subject in a visual field of an eye of the user and obtains a visual field image, and a line-of-sight detecting camera 62 that captures an image of an eye of the user and obtains the image of the eye. The visual field camera 61 is located so as to be positioned near the left eye and/or the right eye when the head-mounted terminal 60 is mounted on the head of the user. In this example, visual field cameras 61 are located near the left eye and near the right eye, respectively, to obtain a stereo image that is made up of a visual field image of the left eye and a visual field image of the right eye, so that a relative three-dimensional positional relationship between each of the user's left eye and right eye and the display unit 31 can be calculated. The line-of-sight detecting camera 62 is located so that each of the left eye and the right eye becomes an imaging target when the head-mounted terminal 60 is mounted on the head of the user. A plurality of line-of-sight detecting cameras 62 (for example, two line-of-sight detecting cameras: a line-of-sight detecting camera for capturing an image of the left eye and a line-of-sight detecting camera for capturing an image of the right eye) may be provided to detect a line of sight reliably and stably.

An apparatus operation method using the apparatus operation device 30 of this embodiment can be executed almost similarly to the process described above by using FIG. 6 in the first embodiment. In the second embodiment, in line-of-sight detection by the line-of-sight detecting unit 42 (step S104 in FIG. 6), a line-of-sight position of the user is calculated based on visual field images obtained by the visual field cameras 61 of the head-mounted terminal 60 and images of the eyes obtained by the line-of-sight detecting cameras 62 of the head-mounted terminal 60.

The head-mounted terminal 60 of this example continues to transmit visual field images obtained by the visual field cameras 61 and images of the eyes obtained by the line-of-sight detecting cameras 62 to the arithmetic unit 34, which is a main body unit. For example, the head-mounted terminal 60 transmits the visual filed images and the images of the eyes as still images at a regular or irregular time interval. The head-mounted terminal 60 may transmit the visual filed images and the images of the eyes as motion pictures at a regular frame rate.

The line-of-sight detecting unit 42 of the arithmetic unit 34 calculates, based on visual field images (in this example, both a visual field image of the left eye and a visual field image of the right eye), a relative positional relationship between the eyes of the user and the screen of the display unit 31. In addition, the line-of-sight detecting unit 42 of the arithmetic unit 34 calculates, based on images of the eyes (in this example, both an image of the left eye and an image of the right eye), a relative positional relationship between a reference point and a movable point of the eyes (a portion that moves relative to the reference point). In a case where the line-of-sight detecting camera 62 captures an image by using visible light, for example, the inner corner and/or the outer corner of an eye is regarded as a reference point and the iris is regarded as a movable point. In a case where the line-of-sight detecting camera 62 captures an image by using infrared light, for example, the corneal reflection point is regarded as a reference point and the pupil is regarded as a movable point.

Subsequently, the line-of-sight detecting unit 42 of the arithmetic unit 34 calculates, based on the calculated relative positional relationship between the eyes and the screen of the display unit 31 and the calculated positional relationship between the reference points and the movable points of the eyes, coordinates indicating a position at which the user is looking in a visual field image (a line-of-sight position in the visual field image). That is, the visual field image and the line-of-sight position are associated with each other.

Figure 12A:
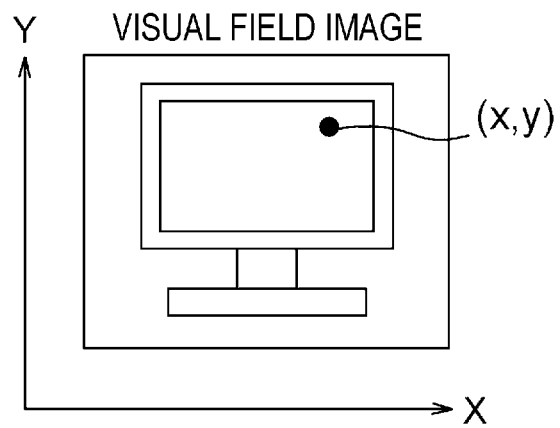
FIGS. 12A to 12C are explanatory diagrams for describing an example of detection of a line of sight and determination of an operation in the apparatus operation device according to the second embodiment.
Figure 12B:
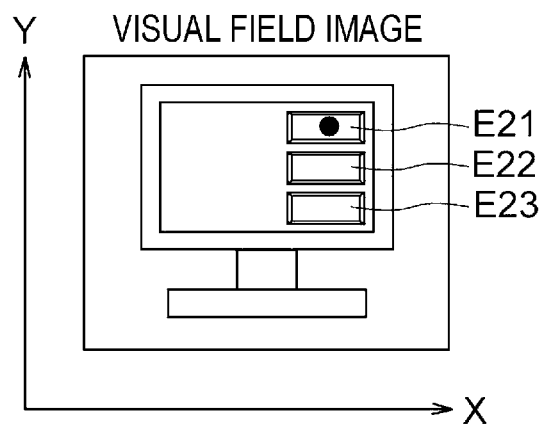
Figure 12C:
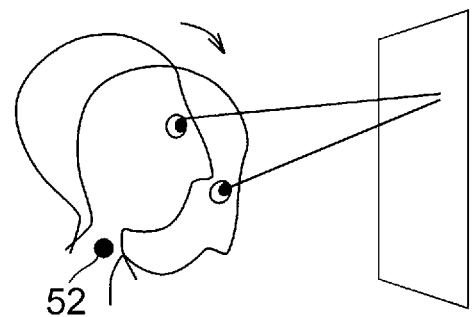

As illustrated in FIG. 12A, in a case where the horizontal direction of a visual field image is an X direction and the vertical direction is a Y direction, a line-of-sight position is represented as a range of a small circle having a certain radius and centered around the (x, y) coordinates. That is, as illustrated in FIG. 12B, it can be determined that the line of sight of the user is directed at a GUI element existing at a portion centered around the (x, y) coordinates in the visual field image (in the figure, the element E21 among three elements: the elements E21 to E23). As illustrated in FIG. 12C, if the user shakes the head vertically while gazing at the GUI element, a motion of the neck is detected by the neck motion sensor 52 of the neck-mounted terminal 33 and a vertical shake of the head (also referred to as "nod") of the user is recognized by the action recognizing unit 43. Accordingly, an operation corresponding to the element E21 that the user has gazed at is decided on.

According to this embodiment, line-of-sight detection is performed by using a so-called glasses-like head-mounted terminal 60. Thus, a line-of-sight position of a user can be accurately detected regardless of the orientation of the face or body of the user. That is, the user can naturally cast the eyes. Even if an angle of the head (the orientation of the face) of the user changes, line-of-sight detection can be accurately performed regardless of the change in the angle of the head.

Example of Application to Medical System

Figure 13:
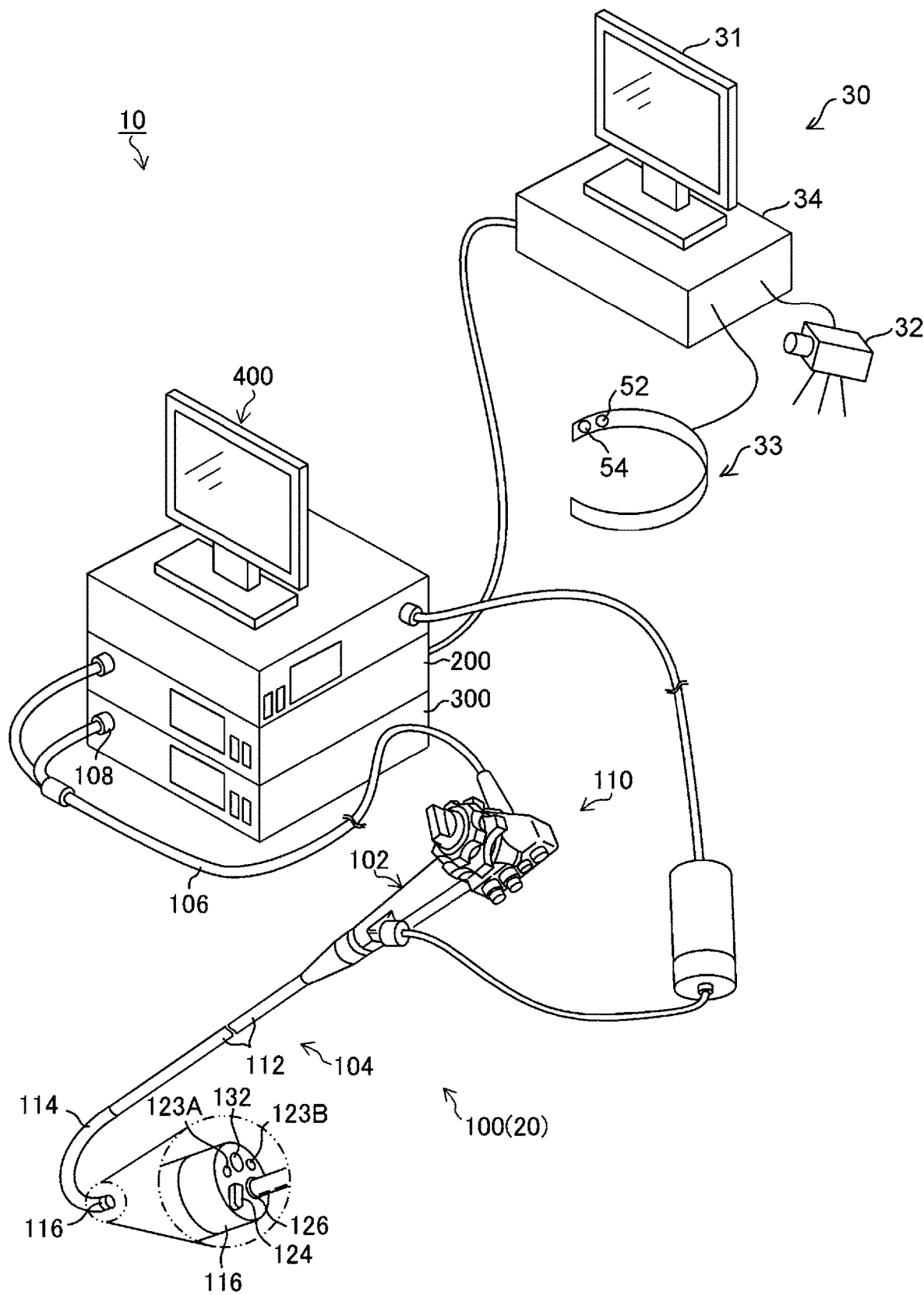
FIG. 13 is a diagram illustrating the overall configuration of an example of an electronic apparatus system in a case where an endoscope apparatus is used as an electronic apparatus.

FIG. 13 is an external view illustrating an electronic apparatus system (an endoscope system 10) in the case of using an endoscope apparatus 100 as each of the electronic apparatuses 20 illustrated in FIG. 1.

Configuration of Endoscope Main Body

An endoscope main body 110 includes a handheld operation section 102 and an insertion section 104 that is connected to the handheld operation section 102. An operator operates the handheld operation section 102 while grasping handheld operation section 102 and inserts the insertion section 104 into a body of a subject to perform observation. The insertion section 104 is constituted by a flexible portion 112, a bending portion 114, and a distal end portion 116, which are arranged in this order from the handheld operation section 102 side. The distal end portion 116 is provided with an imaging optical system 130 (see FIG. 14), an illumination unit 123, a water supply nozzle 124, a forceps port 126, and so forth.

At the time of observation or treatment, an operation of an operation unit 208 (see FIG. 14) enables either or both of visible light and infrared light to be emitted from illumination lenses 123A and 123B of the illumination unit 123. In addition, an operation of the operation unit 208 enables washing water to be ejected from the water supply nozzle 124, so that a lens 132 of the imaging optical system 130 and the illumination lenses 123A and 123B can be washed. The forceps port 126 allows a treatment tool, which is used to extirpate or remove a tumor and which is not illustrated, to be inserted therethrough, and accordingly necessary treatment can be given to a subject by moving the treatment tool forward or backward as appropriate.

Figure 14:
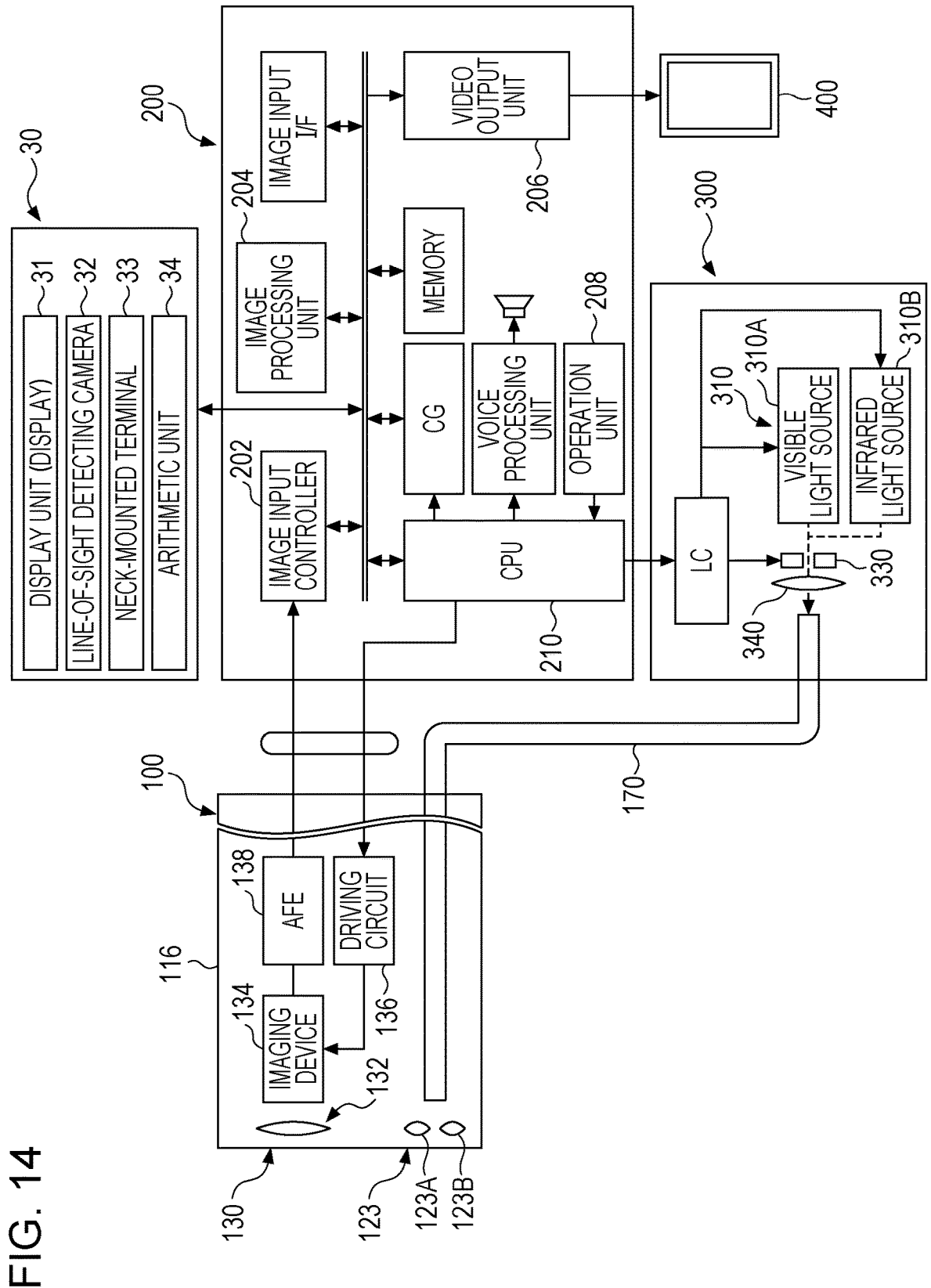
FIG. 14 is a block diagram illustrating the configuration of the electronic apparatus system illustrated in FIG. 13.

As illustrated in FIG. 14, the lens 132 of the imaging optical system 130 is disposed on a distal end surface of the distal end portion 116. An imaging device 134 of a complementary metal-oxide semiconductor (CMOS) type, a driving circuit 136, and an analog front end (AFE) 138 are disposed behind the lens 132, so as to output an image signal. In this embodiment, a description will be given of a case where the imaging device 134 is a CMOS type imaging device, but the imaging device 134 may be of a charge coupled device (CCD) type.

An observation image that has been taken through the lens 132 and so forth is formed on a light reception surface of the imaging device 134, converted into an electric signal, output to an endoscope processor 200 through a signal cable that is not illustrated, and converted into a video signal. Accordingly, the observation image is displayed on a monitor 400, which is connected to the endoscope processor 200.

Display of Observation Image

Figure 15:
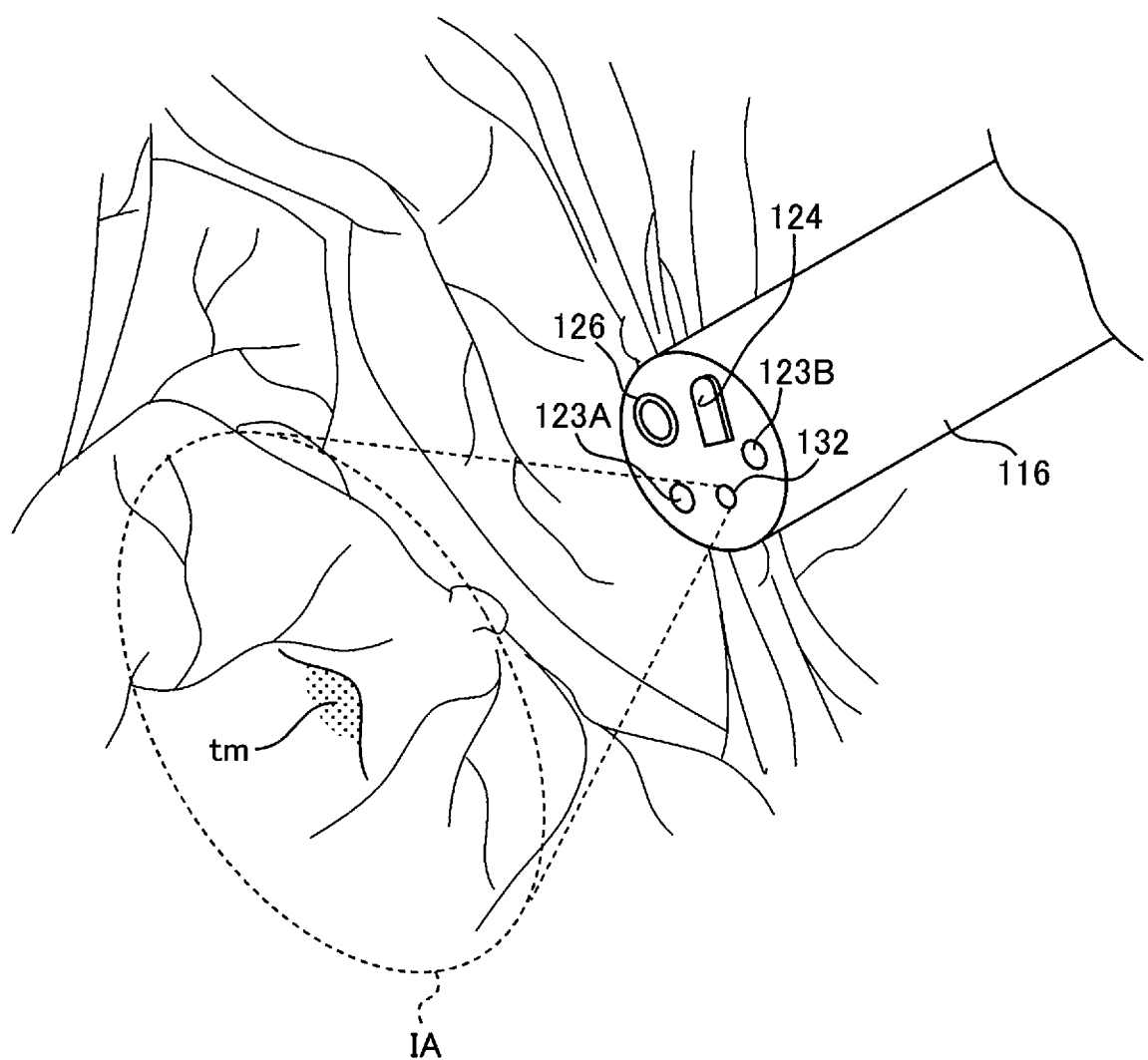
FIG. 15 is a diagram illustrating a state of observation using the endoscope apparatus.

FIG. 15 is a diagram illustrating a state where the insertion section 104 of the endoscope apparatus 100 is inserted into a subject, and illustrating a state where an observation image is obtained via the imaging optical system 130. In FIG. 15, a reference symbol IA denotes an imaging range and a reference symbol tm denotes a tumor (a black raised portion in FIG. 15).

As illustrated in FIGS. 13 to 15, the illumination lens 123A (for visible light) and the illumination lens 123B (for infrared light) of the illumination unit 123 are disposed next to the lens 132 on the distal end surface of the distal end portion 116. An emission end of a light guide 170, which will be described below, is disposed behind the illumination lenses 123A and 123B. The light guide 170 is inserted through the insertion section 104, the handheld operation section 102, and a universal cable 106, and an incidence end of the light guide 170 is located in a light guide connector 108.

Configuration of Light Source Device

As illustrated in FIG. 14, a light source device 300 is constituted by a light source 310, a diaphragm 330, a condenser lens 340, and so forth, and causes illumination light to enter the light guide 170. The light source 310 includes a visible light source 310A and an infrared light source 310B and is capable of emitting one or both of visible light and infrared light. Accordingly, with the light guide connector 108 (see FIG. 13) being connected to the light source device 300, illumination light emitted by the light source device 300 is transmitted to the illumination lenses 123A and 123B through the light guide 170 and is applied to an observation range from the illumination lenses 123A and 123B.

Configuration of Endoscope Processor

Next, the configuration of the endoscope processor 200 will be described with reference to FIG. 14. In the endoscope processor 200, an image input controller 202 receives an image signal output from the endoscope apparatus 100, an image processing unit 204 performs necessary image processing thereon, and a video output unit 206 outputs a resulting image signal. Accordingly, an observation image is displayed on the monitor 400. These processes are performed under control of a central processing unit (CPU) 210. The image processing unit 204 performs, in addition to image processing such as white balance adjustment, switching or superimposition of an image displayed on the monitor 400, electronic zoom processing, display and switching of an image according to an operation mode, or extraction of a specific component (for example, a brightness signal) from an image signal.

The endoscope processor 200 includes the operation unit 208. The operation unit 208 includes an operation mode setting/selecting switch, a water supply instruction button, or the like (not illustrated), and is capable of performing an operation of emitting visible light or infrared light.

Others

A description has been given of a case where the target apparatus to be operated is the endoscope apparatus 100, which is a medical apparatus, with reference to FIG. 13. However, the target apparatus to be operated in the present invention is not necessarily a medical apparatus. The embodiments are applicable to an operation of a mobile apparatus, such as a smartphone, a tablet terminal, or a game machine, as well as a medical apparatus, and to an operation of an apparatus under a situation where it is impossible to freely use both hands while operating an apparatus, for example, driving a car, or a situation where the arrangement of an apparatus is restricted. The target apparatus to be operated is not limited to a single apparatus. One of a plurality of apparatuses may be selected by using a line of sight and a motion of the neck. In the present invention, a gesture may be performed by moving only the neck without moving the head, depending on the target apparatus to be operated, the usage situation of the apparatus, the type or importance of an operation, or the like. A user as a target of line-of-sight detection and a user as a target of gesture detection may be different from each other.

Obviously, the present invention is not limited to the above-described embodiments, and various changes can be made without deviating from the gist of the present invention.

REFERENCE SIGNS LIST 10 electronic apparatus system
20 electronic apparatus
22 database (an example of a voice recording unit)
30 apparatus operation device
31 display unit
32 line-of-sight detecting camera
33 neck-mounted terminal
34 arithmetic unit
38 communication unit
39 storage unit (an example of a voice recording unit)
40 CPU
41 display control unit
42 line-of-sight detecting unit
43 action recognizing unit
44 determining unit
45 voice recognizing unit
46 apparatus control unit
52 neck motion sensor
54 vibration sensor
60 head-mounted terminal
61 visual field camera
62 line-of-sight detecting camera

What is claimed is:

1. An apparatus operation device comprising:
a processor; and
a neck-mounted terminal that is mounted around a neck of the user and detects a motion of the neck of the user;
wherein the processor is configured to:
detect a line of sight of a user, based on the line of sight that has been detected and the motion of the neck that has been detected,
determine a target apparatus to be operated among a plurality of apparatuses and operation details for the target apparatus;
control the target apparatus in accordance with the determination,
suspend detection of the line of sight upon detection of the motion of the neck being started by the neck-mounted terminal, and
start the detection of the line of sight upon the detection of the motion of the neck being finished by the neck-mounted terminal.

2. The apparatus operation device according to claim 1, wherein the processor
determines, based on the line of sight that has been detected, at least one of the target apparatus or the operation details, and
confirms the determination, based on the motion of the neck that has been detected.

3. The apparatus operation device according to claim 2, wherein
the processor detects a movement of the line of sight, and the processor determines, based on the movement of the line of sight that has been detected, at least one of the target apparatus or the operation details.

4. The apparatus operation device according to claim 3, wherein the operation details include a function that the processor causes the target apparatus to execute, and an execution condition for the function.

5. The apparatus operation device according to claim 3, wherein the processor recognizes a voice of the user by using a vibration of a throat of the user, the vibration being detected by the neck-mounted terminal.

6. The apparatus operation device according to claim 2, wherein the operation details include a function that the processor causes the target apparatus to execute, and an execution condition for the function.

7. The apparatus operation device according to claim 6, wherein the processor recognizes a voice of the user by using a vibration of a throat of the user, the vibration being detected by the neck-mounted terminal.

8. The apparatus operation device according to claim 2, wherein the processor recognizes a voice of the user by using a vibration of a throat of the user, the vibration being detected by the neck-mounted terminal.

9. The apparatus operation device according to claim 1, wherein
the processor detects a movement of the line of sight, and
the processor determines, based on the movement of the line of sight that has been detected, at least one of the target apparatus or the operation details.

10. The apparatus operation device according to claim 9, wherein the processor recognizes a voice of the user by using a vibration of a throat of the user, the vibration being detected by the neck-mounted terminal.

11. The apparatus operation device according to claim 9, wherein the operation details include a function that the processor causes the target apparatus to execute, and an execution condition for the function.

12. The apparatus operation device according to claim 1, wherein the operation details include a function that the processor causes the target apparatus to execute, and an execution condition for the function.

13. The apparatus operation device according to claim 12, wherein the processor recognizes a voice of the user by using a vibration of a throat of the user, the vibration being detected by the neck-mounted terminal.

14. The apparatus operation device according to claim 1, wherein the processor recognizes a voice of the user by using a vibration of a throat of the user, the vibration being detected by the neck-mounted terminal.

15. The apparatus operation device according to claim 14, comprising:
a voice recording unit that records the voice that has been recognized.

16. The apparatus operation device according to claim 1, wherein the processor invalidates detection of the line of sight if the motion of the neck that has been detected is larger than a threshold of an amount of motion or a threshold of an amount of fluctuation of a direction of motion.

17. An electronic apparatus system comprising:
the apparatus operation device according to claim 1; and
an electronic apparatus which is the target apparatus.

18. The electronic apparatus system according to claim 17, wherein the electronic apparatus is a medical apparatus.

19. An apparatus operation method for an apparatus operation device comprising a processor configured to detect a line of sight of a user and a neck-mounted terminal that is mounted around a neck of the user and detects a motion of the neck of the user, the apparatus operation method comprising:
a determination step of determining, based on the line of sight that has been detected and the motion of the neck that has been detected, a target apparatus to be operated among a plurality of apparatuses and operation details for the target apparatus;
a control step of controlling the target apparatus in accordance with the determination in the determination step,
suspending the detection of the line of sight upon detection of the motion of the neck being started by the neck-mounted terminal, and
starting the detection of the line of sight upon the detection of the motion of the neck being finished by the neck-mounted terminal.

\* \* \* \* \*